United States Patent [19]
Harrington et al.

[11] Patent Number: 5,543,510
[45] Date of Patent: Aug. 6, 1996

[54] PROCESS AND INTERMEDIATES FOR THE PREPARATION OF (+)-HYDANTOCIDIN AND ANALOGS THEREOF

[75] Inventors: Philip M. Harrington, Cranbury, N.J.; Michael E. Jung, Los Angeles, Calif.

[73] Assignee: American Cyanamid Company, Madison, N.J.

[21] Appl. No.: 262,411

[22] Filed: Jun. 20, 1994

Related U.S. Application Data

[62] Division of Ser. No. 140,580, Oct. 21, 1993, Pat. No. 5,354,868.

[51] Int. Cl.$^6$ ................................................ C07H 15/02
[52] U.S. Cl. ............................................................ 536/53
[58] Field of Search ................................................ 536/53

[56] References Cited

U.S. PATENT DOCUMENTS

| | | | |
|---|---|---|---|
| 4,320,135 | 3/1982 | Kathawala | 548/301.4 |
| 4,952,234 | 8/1990 | Haneishi | 548/309 |

FOREIGN PATENT DOCUMENTS 4129728 of 0000 Germany.

OTHER PUBLICATIONS

Nakajima, M.; Takamatsu, Y.; Kinoshita, T.; Kawakubo, K.; Shindo, M.; Honma, T.; Tohjigmori, M.; Haneishi, T. Journal of Antibiotics 1991, 44,293.

Mio, S.; Ichinose, R.; Goto, K.; Sugai, S. Tetrahedron 1991, 47,2111.

Mio, S.; Kumagawa, Y.; Sugai, S. Tetrahedron 1991, 47,2133.

Haruyama H.; Takayama, T.; Kinoshita, T.; Kondo, M.; Nakajima, M.; Haneishi, T. Journal Chemical Society, Perkin Trans. 1 1991, 1637.

Mio, S.; Hiromi, S.; Shindou, M.; Honma, T.; Sugai, S. Agricultural and Biological Chemistry 55 (4), 1105–1109, 1991.

Mio, S.; and Sugai, S. Sankyo Kenkyusho Nempo 43, 133–139 (1991).

Mio, S.; Ueda, M.; Hamura, M.; Kitagawa J.; Sugai, S. Tetrahedron 1991, 47,2145.

Mio S.; Shiraishi, M.; Sugai, S. Tetrahedron 1991 47,2121.

Buffel, J. O. C. 49 2165 (1984).

*Primary Examiner*—Robert Gerstl
*Attorney, Agent, or Firm*—John W. Hogan, Jr.

[57] ABSTRACT

Hydantocidin is a potent non-selective herbicidal natural product. This invention provides an efficient method for the enantioselective preparation of (+)-hydantocidin, analogs thereof and intermediates therefor.

3 Claims, No Drawings

PROCESS AND INTERMEDIATES FOR THE PREPARATION OF (+)-HYDANTOCIDIN AND ANALOGS THEREOF

This is a divisional of application Ser. No. 08/140,580 filed on Oct. 21, 1993, now U.S. Pat. No. 5,354,868.

BACKGROUND OF THE INVENTION

Herbicides which demonstrate potent total vegetation control over a broad spectrum of annual and perennial weeds are of high interest in agricultural practice. Accordingly, there is an ongoing search in the art to discover new and effective herbicides. (+)-Hydantocidin, produced from *Streptomyces hygroscopicus* which was isolated from a soil sample collected in Japan, has demonstrated herbicidal activity at levels comparable to commercial standards such as glyphosate and bialaphos and has also been shown to be non-toxic to mammals (c.f. Nakajima, M.; Itoi, K.; Takamatsu, Y.; Kinoshita, T.; Okazaki, T.; Kawakubo, K.; Shindo, M.; Honma, T.; Tohjigamori, M.; Haneishi, T. Journal of Antibiotics 1991, 44,293.).

The use of (+)-hydantocidin as a herbicide is described in U.S. Pat. No. 4,952,234. A process for the preparation of said compound is described in DE 4,129,728. Two complimentary syntheses of (+)-hydantocidin are Mio, S.; Ichinose, R.; Goto, K.; Sugai, S. Tetrahedron 1991, 47,2111 and Mio, S.; Kumagawa, Y.; Sugai, S. Tetrahedron 1991, 47,2133. However, all of these processes are fundamentally similar and are not economically feasible. In general, many synthetic transformations are required, overall yields are low, and chemical selectivity is lacking.

It is, therefore, an object of the present invention to provide a simple and efficient enantioselective process for the preparation of (+)-hydantocidin.

It is another object of this invention to provide intermediate compounds useful in the preparation of hydantocidin and derivatives thereof.

It is a further object of this invention to provide thiohydantocidin compounds which are useful as herbicidal agents.

SUMMARY OF THE INVENTION

There is provided a process for the preparation of a compound of formula I

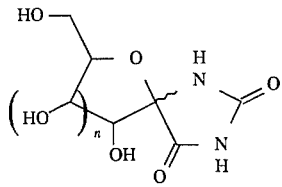

wherein X is O or S and n is an integer of 1 or 2 which comprises hydrating a compound of formula II

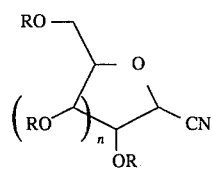

wherein n is an integer of 1 or 2 and R is a protecting group in the presence of manganese dioxide and a solvent to form an intermediate compound of formula III

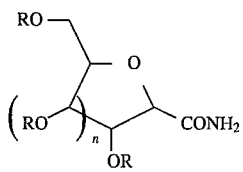

brominating the formula III compound to form a second intermediate of formula IV

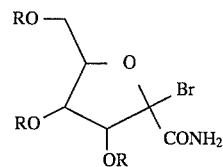

reacting the second intermediate with silver cyanate or silver thiocyanate in the presence of an anhydrous non-protic solvent at a temperature of about 75°–150° C. to form a third intermediate of formula V

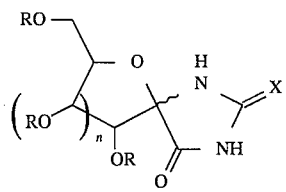

wherein X is O or S and deprotecting the formula V intermediate in the presence of a base to obtain the desired compound of formula I.

There are also provided intermediate compounds of formulas III, IV and V, useful in the preparation of hydantocidin.

Further provided is an herbicidal compound having the structure

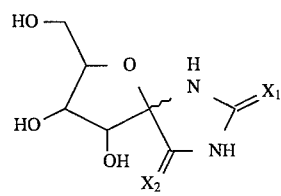

wherein $X_1$ and $X_2$ are independently O or S provided at least one must be S, the optical isomers thereof and the diastereomers thereof.

DESCRIPTION OF INVENTION

The present invention relates to an efficient and enantioselective preparation of the herbicidal natural product (+)-hydantocidin (D-ribose-1-spiro-5'-$N^{1'}$-β-hydantoin), carbohydrate-based derivatives thereof and sulfur analogs thereof.

Advantageously, the inventive process employs commercially available sugars as starting materials and efficiently converts the starting sugar to the desired final product of formula I with retention of the stereochemistry of the sugar moiety.

In accordance with the process of the invention, a compound of formula I

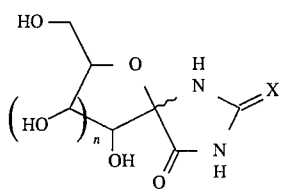

wherein X is O or S and n is an integer of 1 or 2; the optical isomers thereof and the diastereomers thereof may be prepared by hydrating a readily available sugar derivative of formula II

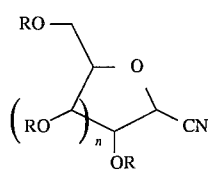

wherein n is an integer of 1 or 2 and R is a protecting group in the presence of manganese dioxide and a solvent to form the corresponding amide compound, brominating said amide to form the desired 1-bromo-1-amide sugar intermediate, spirocyclizing the 1-bromo-1-amide sugar with silver cyanate or silver thiocyanate at a temperature of about 75°–150° C. in the presence of an anhydrous non-protic solvent to form the spirocycle intermediate and deprotecting said intermediate in the presence of a base.

The process of the invention is shown in flow diagram I, wherein n is an integer of 1 or 2; R is a protecting group and X is O or S.

Compounds of the invention having the structure

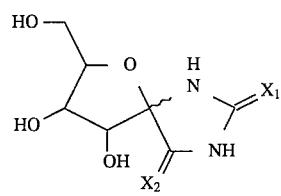

wherein $X_2$ is S and $X_1$ is O or S may be prepared by hydrating the appropriate sugar derivative of formula IIa wherein n is an integer of 1 and R is a protecting group in the presence of manganese dioxide to form the corresponding amide compound of formula IIIa and reacting the amide with Lawesson's reagent (Tetrahedron Let., 1980, 21,4061) or $P_2S_5$ to form the corresponding thioamide. The thioamide may then be carried on to the desired product using the procedures described hereinabove. The conversion is shown in flow diagram II.

Flow Diagram I

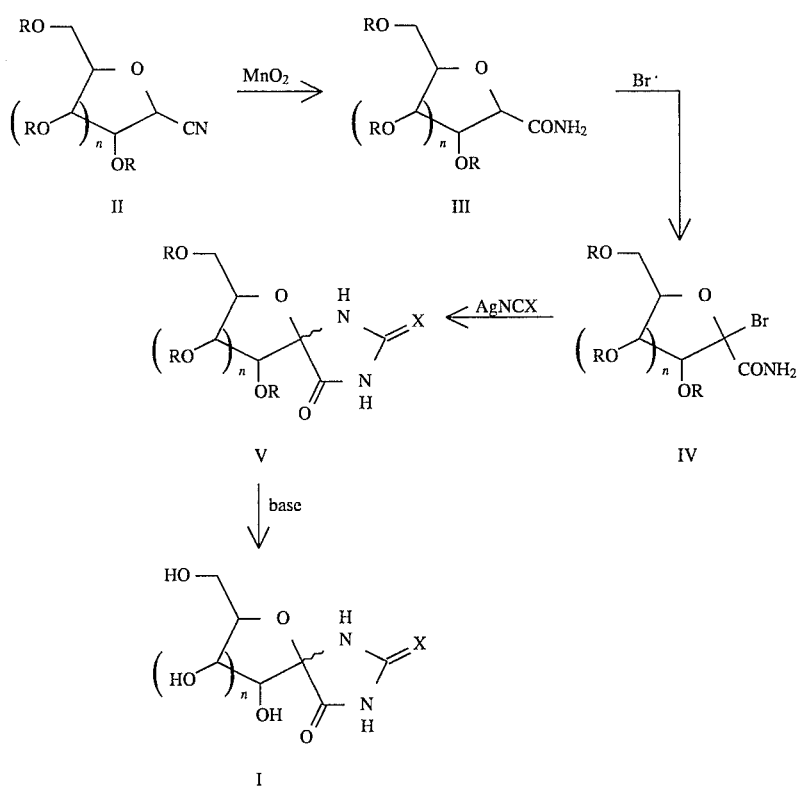

Flow Diagram II

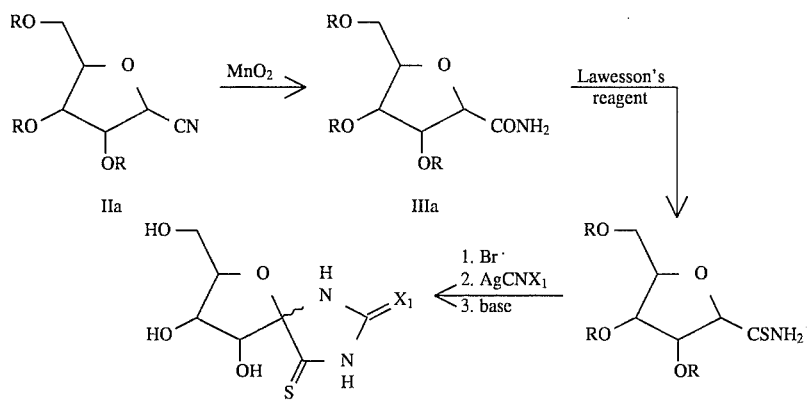

The term protecting group as used in the specification and claims designates those groups well known in the art to selectively block an hydroxyl functionality, for example, sulfonyl groups such as methylsulfonyl, trifluoromethylsulfonyl, p-toluenesulfonyl and the like; ether groups such as methoxymethyl, benzyl, halobenzyl, methylthiomethyl, benzyloxymethyl, tetrahydrofuranyl and the like; silyl ether groups such as trimethylsilyl, triethylsilyl, triisopropylsilyl, dimethylisopropylsilyl, diethylisopropylsilyl, t-butyldimethylsilyl, t-butyldiphenylsilyl, triphenylsilyl and the like; ester groups such as formate, acetate, chloroacetate, dichloroacetate, trichloroacetate, methoxyacetate, triphenylmethoxyacetate, phenoxyacetate, 3-phenylpropionate, pivaloate, benzoate, 2,4,6-trimethylbenzoate, halobenzoate, nitrobenzoate and the like; carbonate groups and carbamate groups.

Preferred protecting groups for use in the method of invention are ester groups such as acetate, benzoate and nitrobenzoate and ether goups such as benzyl, halobenzyl and nitrobenzyl.

Glycosyl cyanides of formula II and their preparation are well known in the art. A typical method of preparation is Utimoto, K.; Wakabayashi, Y.; Horiie, T., Inoue, M.; Shishiyama, Y.; Obayishi, M.; Nozaki, H., Tetrahedron 1983, 39,967.

Solvents suitable for use in the manganese dioxide hydration of the formula II glycosyl cyanide are organic solvents such as halogenated hydrocarbons, e.g. methylene chloride, 1,2-dichloroethane and 1,1,1-trichloroethane; esters such as ethyl acetate, aromatic hydrocarbons such as benzene and toluene, ethers such as diethyl ether and dioxane and the like. Preferred solvents are halogenated hydrocarbons and aromatic hydrocarbons, most preferred are methylene chloride and toluene. It is understood, the manganese dioxide reagent used in the method of invention contains traces of water.

Brominating agents suitable for use in the inventive method are any conventional reagent useful for generating a bromine free radical such as N-bromosuccinimide or bromine. The preferred solvent for use in the bromination step is carbon tetrachloride.

Solvents suitable for use in the spirocyclzation of the 1-bromo-1-amide compound of formula IV are any non-protic, anhydrous solvents having a boiling point greater than 70° C., preferably nitromethane. Suitable reaction temperatures for the spirocyclization are about 75°–150° C., preferably about 80°–100° C.

The formula V compounds may be deprotected under basic conditions to yield the product formula I compound. The appropriate base will vary depending upon the nature of the protecting group. Surprisingly, when R is benzoyl, the formula V compound may be treated with aqueous lithium peroxide to yield the desired forumula I compound with complete retention of stereochemistry and when R is acetyl, the formula V compound may be effectively deprotected using ammonia gas in methanol with complete retention of stereochemistry.

In a preferred embodiment of the invention, the formula I product obtained is the β anomer of the D isomer. The D configuration may be conferred by the appropriate selection of the starting sugar derivative of formula II. The spirocyclization with silver cyanate or silver thiocyanate yields a mixture of the β and α anomers of formula V, designated Va and Vb, respectively. The diastereomeric products may be separated using conventional chromatographic procedures such as flash chromatography or liquid chromotography. Advantageously, the inventive process favors the formation of the β anomer. The α anomer may be converted to an equilibrium mixture of α and β anomers by treatment with a protic solvent and an organic acid. For example, treatment of Vb with an 0.05N methanolic solution of camphorsulfonic acid (CSA) yields an equilibrium mixture wherein the β anomer Va is the major component.

Using D-ribose as the starting sugar, the enantioselective inventive process is shown in flow diagram III.

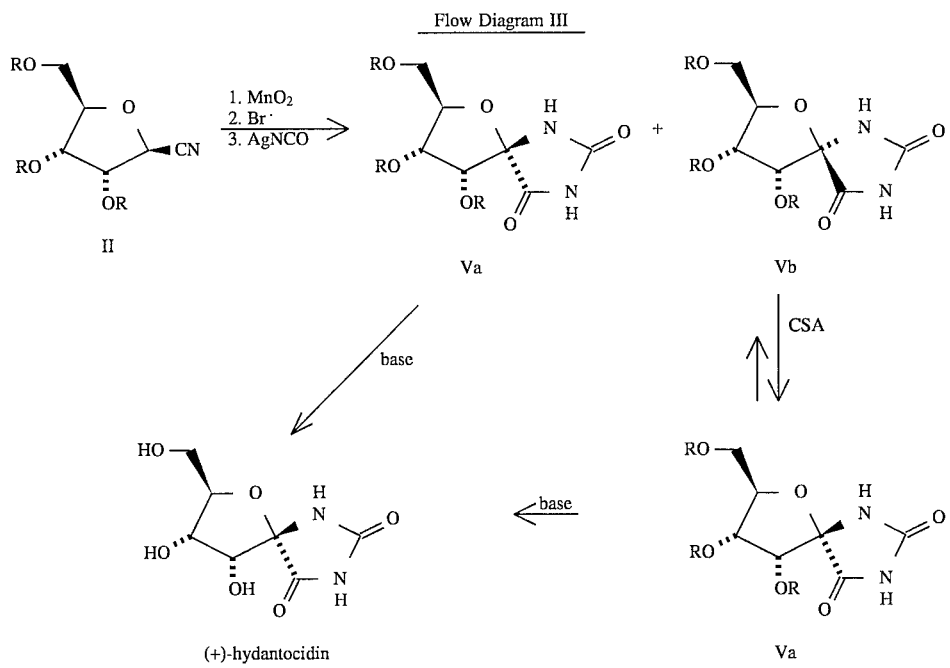

Flow Diagram III

It has now been found that a compound having the following structure

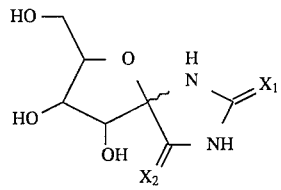

wherein $X_1$ and $X_2$ are independently O or S provided that at least one must be S is an effective herbicidal agent which controls both broadleaf and grass weed species. In general, the above compound is suitable for use as a broad spectrum herbicide when applied postemergence to the locus in which the weed control is desired.

In order to facilitate a further understanding of the invention, the following examples are presented primarily for the purpose of illustrating more specific details thereof. The invention is not to be deemed limited thereby except as defined in the claims. The terms $^1$HNMR and $^{13}$CNMR designate proton and carbon 13 nuclear magnetic resonance, respectively. The terms MS and IR designate mass spectral and infrared, respectively.

EXAMPLE 1

Preparation of
2,3,5-tri-O-benzoyl-β-D-ribofuranosyl amide

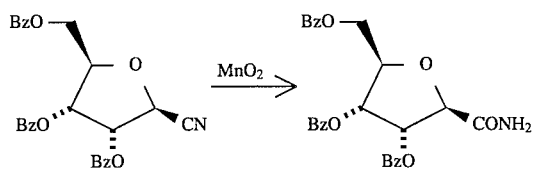

A solution of 3.34 g (7.1 mmol) of 2,3,5-tri-O-benzoyl-β-D-ribofuranosyl cyanide in methylene chloride is charged with 16.70 g (192 mmol) of manganese(IV) oxide, stirred vigorously at ambient temperatures for 24 h and vacuum filtered through a Celite pad. The filtrate is concentrated under reduced pressure to give a residue which is purified by flash column chromatography. (1:2 ethyl acetate:hexanes) The title product is obtained as a white foam 1.87 g (54% y) mp 58° C., identified by $^1$HNMR, $^{13}$CNMR, MS, and IR analyses.

EXAMPLE 2

Preparation of
2,3,4,6-tetra-O-acetyl-βD-galactopyranosyl amide

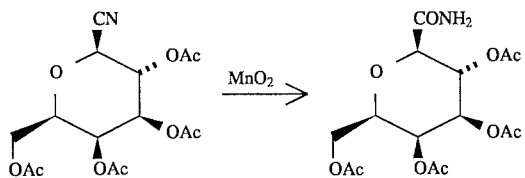

A solution of 4.85 g (13.6 mmol) of 2,3,4,6-tetra-O-acetyl-β-D-galactopyranosyl cyanide in methylene chloride is charged with 24.25 g (279 mmol) of manganese(IV) oxide, stirred vigorously at ambient temperatures for 70 h and vacuum filtered through a Celite pad. The filtrate is concentrated under reduced pressure to give a residue which is purified by flash column chromatography. (70% ethyl acetate/hexanes to ethyl acetate gradient) The title product is obtained as a white foam, 1.60 g (31% y) identified by $^1$HNMR and MS analyses.

EXAMPLE 3

Preparation of
2,3,5-tri-O-benzoyl-1-bromo-β-D-ribofuranosyl amide

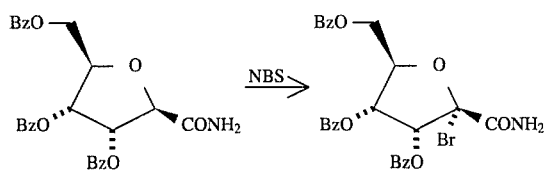

A warm solution of 1.54 g (3.1 mmol) of 2,3,5-tri-O-benzoyl-β-D-ribofuranosyl amide in carbon tetrachloride is charged with 0.67 g (3.8 mmol) of N-bromosuccinimide and 0.08 g (0.3 mmol) of benzoyl peroxide. The reaction mixture is refluxed for 2 h, cooled, and concentrated under reduced pressure to give a residue. Purification of the residue is carried out by flash column chromatography. (30% ethylacetate/hexanes) The title product is obtained as a white foam 0.91 g (51% y) mp 63° C., identified by $^1$HNMR, $^{13}$CNMR, MS, and IR analyses.

EXAMPLE 4

Preparation of
2,3,6-tetra-O-acetyl-1-bromo-β-D-galactopyranosyl amide

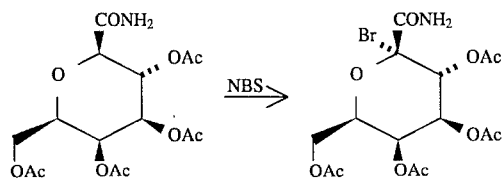

A warm solution of 0.92 g (2.4 mmol) of 2,3,6-tetra-O-acetyl-β-D-galactopyranosyl amide in carbon tetrachloride is charged with 0.53 g (3.0 mmol) of N-bromosuccinimide and 0.06 g (0.2 mmol) of benzoyl peroxide. The reaction mixture is refluxed for 2 h, cooled, and concentrated under reduced pressure to give a residue. Purification of the residue is carried out by flash column chromatography. (50% to 70% ethyl acetate/hexanes gradient) The title product is obtained as a white foam, 1.00 g (90% y) identified by $^1$HNMR, $^{13}$CNMR and MS analyses.

EXAMPLE 5

Preparation of
2,3,5-tri-O-benzoyl-D-ribose-1-spiro-5'-N$^{1'}$-β-hydantoin and
2,3,5-tri-O-benzoyl-D-ribose-1-spiro-5'-N$^{1'}$-α-hydantoin

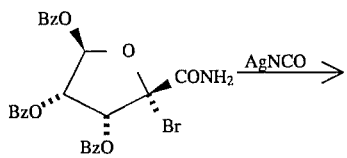

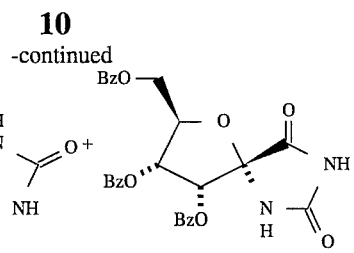

A mixture of 0.81 g (1.4 mmol) of 2,3,5-tri-O-benzoyl-1-bromo-β-D-ribofuranosyl amide and 3.24 g of activated 3 Å sieves in distilled nitromethane is incubated with stirring, under a nitrogen atmosphere, at ambient temperatures for 1 h. The mixture is treated, in one portion, with 0.85 g (5.7 mmol) of silver cyanate, heated at 80° C. for 2 h, cooled and filtered. The filtrate is concentrated in vacuo to give a residue. The residue is purified by flash column chromatography. (10% ethyl acetate/methylene chloride) The title products are obtained as white foams: the β-hydantoin (0.23 g, 30% y, mp 87°–90° C.)and the α-hydantoin (0.12 g, 16% y, mp 94°–96° C.), each identified by $^1$HNMR, $^{13}$CNMR, MS an IR analyses.

EXAMPLE 6

Preparation of
2,3,5-tri-O-benzoyl-D-ribose-1-spiro-5'-N$^{1'}$-β-2'-thiohydantoin and
2,3,5-tri-O-benzoyl-D-ribose-1-spiro-5'-N$^{1'}$-α-2'-thiohydantoin

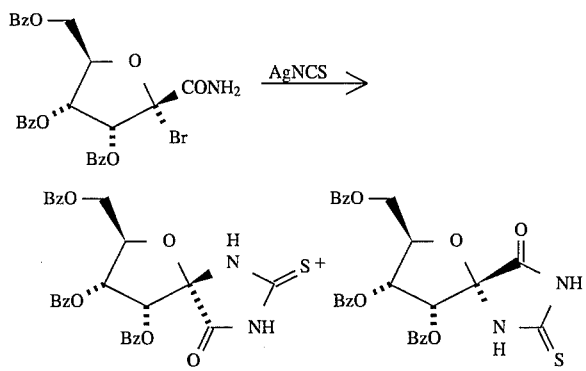

A mixture of 1.59 g (2.8 mmol) of 2,3,5-tri-O-benzoyl-1-bromo-β-D-ribofuranosyl amide and 6.36 g of activated 3 Å sieves in distilled nitromethane is incubated with stirring, under a nitrogen atmosphere at ambient temperature for 1 h. The mixture is treated, in one portion, with 1.86 g (11.2 mmol) of silver thiocyanate, heated at 100° C. for 16 h and vacuum filtered. The filtrate is concentrated to give a residue. Purification of the residue is carried out by flash column chromatography. (20% to 30% ethyl acetate/hexanes gradient) The title products are obtained as yellow foams: the β-thiohydantoin (0.74 g, 48% y, mp 92°–96° C.) and the α-thiohydantoin (0.34 g 22% y mp 91°–95° C.) each identified by $^1$HNMR, $^{13}$CNMR and MS analyses.

EXAMPLE 8

Equilibration of 2,3,5-tri-O-benzoyl-D-ribose-1-spiro-5'-N$^{1'}$-α-hydantoin and 2,3,5-tri-O-benzoyl-D-ribose-1-spiro-5'-N$^{1'}$-β-hydantoin

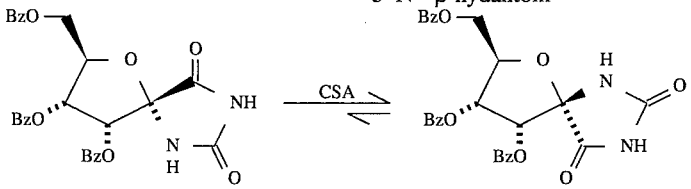

A stirred solution of 0.20 g (0.4 mmol) of 2,3,5-tri-O-benzoyl-D-ribose-1-spiro-5'-N$^{1'}$-α-hydantoin in 10 mL of 0.05N camphorsulfonic acid (CSA, 0.5 mmol) in methyl alcohol is heated at 70° C. for 15 h. After cooling, the reaction mixture is concentrated to a residue under reduced pressure. The residue is purified by flash column chromatography. (10% ethyl acetate/methylene chloride) The title β-hydantoin product is obtained in 80% yield (0.16 g) and the starting title α-hydantoin is recovered (0.02 g), 10% recovery.

EXAMPLE 7

Preparation of 2,3,4,6-tetra-O-acetyl-D-galactose-1-spiro-5'-N$^{1'}$-β-hydantoin and 2,3,4,6-tetra-O-acetyl-D-galactose-1-spiro-5'-N$^{1'}$-α-hydantoin

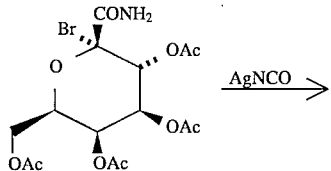

EXAMPLE 9

Equilibration of 2,3,5-tri-O-benzoyl-D-ribose-1-spiro-5'-N$^{1'}$-α-2'-thiohydantoin and 2,3,5-tri-O-benzoyl-D-ribose-1-spiro-5'-N$^{1'}$-β-2'-thiohydantoin

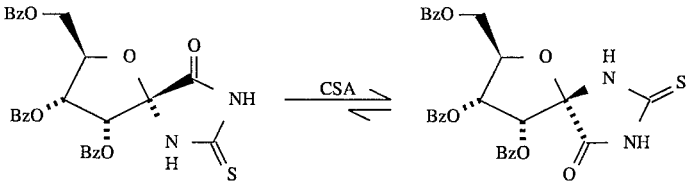

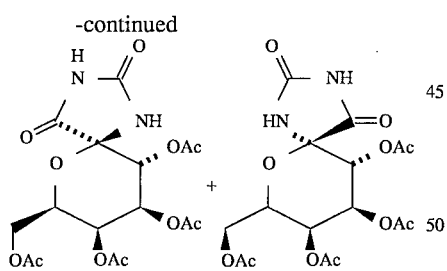

-continued

A stirred solution of 0.88 g (1.6 mmol) of 2,3,5-tri-O-benzoyl-D-ribose-1-spiro-5'-N$^{1'}$-α-2'-thiohydantoin in 20 mL of 0.05N camphorsulfonic acid (CSA, 1.0 mmol) in methyl alcohol is heated at 70° C. for 15 h. After cooling, the reaction mixture is concentrated under reduced pressure. The residue is purified by flash column chromatography. (10% ethyl acetate/methylene chloride) The title β-thiohydantoin is obtained in 43% yield (0.38 g) and the starting title α-thiohydantoin is recovered (0.10 g), 11% recovery.

A mixture of 1.70 g (3.7 mmol) of 2,3,4,6-tetra-O-acetyl-1-bromo-β-D-galactopyranosyl amide and 6.80 g of activated 3 Å sieves in distilled nitromethane is incubated with stirring, under a nitrogen atmosphere, at ambient temperatures for 1 h. The mixture is treated in one portion with 2.24 g (14.9 mmol) of silver cyanate, heated at 80° C. for 2 h and vacuum filtered. The filtrate is concentrated to give a residue. Purification of the residue is carried out by flash column chromatography. (70% to 80% ethyl acetate/hexanes gradient) The title products are obtained as white foams: the β-hydantoin (1.09 g, 70% y) and the α-hydantoin (0.30 g, 19% y), each are identified by $^1$HNMR, $^{13}$CNMR and MS analyses.

EXAMPLE 10

Preparation of D-ribose-1-spiro-5'-N$^{1'}$-β-hydantoin (hydantocidin)

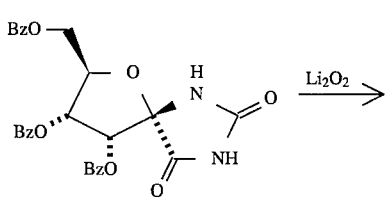

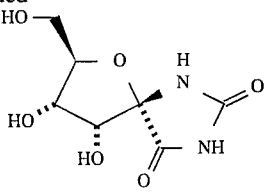

A stirred solution of 0.51 g (1.0 mmol) of 2,3,5-tri-O-benzoyl-D-ribose-1-spiro-5'-N[1']-β-hydantoin in 20 mL of THF:H$_2$O (4:1) is cooled to 0° C. and treated in one portion, with 0.22 g (4.8 mmol) of lithium peroxide. After 1.5 h, the reaction mixture is concentrated under reduced pressure. The concentrate is purified by flash column chromatography. (10% to 20% ethyl acetate/methylene chloride) The title product is obtained as a white powder, 0.19 g (90% y) mp 178°–180° C., $[\alpha]^{25}_D$+28.5°, literature[1] mp 187°–189° C. and literature[1] $[\alpha]^{25}_D$+28.8°.

[1] M. Nakajima et al Journal Of Antibiotics, 1991, 44, 293.

EXAMPLE 11

Preparation of
D-ribose-1-spiro-5'-N[1']-β-2'-thiohydantoin

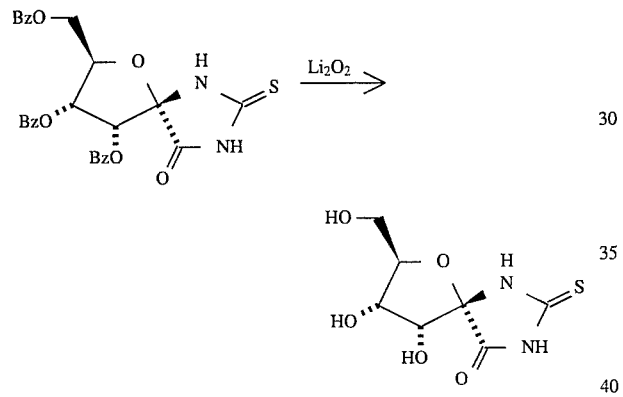

A stirred solution of 0.82 g (1.5 mmol) of 2,3,5-tri-O-benzoyl-D-ribose-1-spiro-5'-N[1']-β-2'-thiohydantoin in 20 mL of THF:H$_2$O (4:1) is cooled to 0° C. and in one portion is treated with 0.34 g (7.4 mmol) of lithium peroxide. After 3 h, the reaction mixture is concentrated under reduced pressure. The concentrate is purified by flash column chromatography. (10% to 20% methyl alcohol/methylene chloride gradient) The title product is obtained as a white powder 0.19 g (54%) mp 83°–86° C., identified by $^1$HNMR, $^{13}$CNMR, and MS analyses.

EXAMPLE 12

Preparation of
D-galactose-1-spiro-5'-N[1']-β-hydantoin

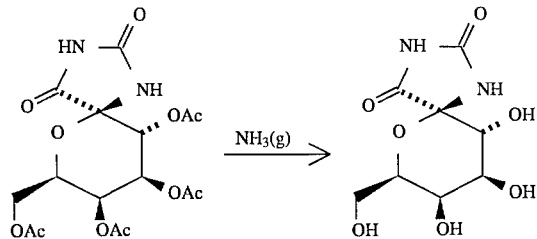

A stirred solution of 0.45 g (1.1 mmol) of 2,3,4,6-tetra-O-acetyl-D-galactose-1-spiro-5'-N[1']-β-hydantoin in 20 mL of methyl alcohol is bubbled through with ammonia gas for 4 h. The reaction mixture is concentrated under reduced pressure. The concentrate is purified by flash column chromatography. (5:3:2 ethyl acetate:isopropyl alcohol:water) The title product is obtained as a white powder 0.21 g (78%) mp 234°–236° C., identified by $^1$HNMR, $^{13}$CNMR, and MS analyses.

EXAMPLE 13

Preparation of
D-galactose-1-spiro-5'-N[1']-α-hydantoin

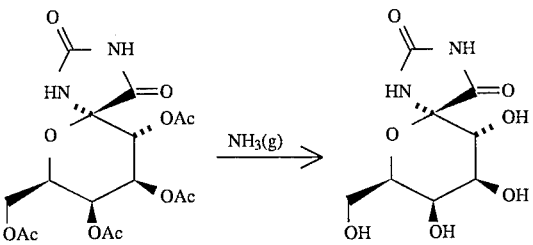

A stirred solution of 0.30 g (0.7 mmol) of 2,3,4,6-tetra-O-acetyl-D-galactose-1-spiro-5'-N[1']-α-hydantoin in 15 mL of methyl alcohol is bubbled through with ammonia gas for 3.5 h. The reaction mixture is concentrated under reduced pressure. The concentrate is purified by flash column chromatography (5:3:2 ethyl acetate:isopropyl alcohol:water) The title product is obtained as a white powder 0.10 g (56%) mp 122°–126° C., identified by $^1$HNNMR, $^{13}$CNMR, and MS analyses.

EXAMPLE 14

Postemergence herbicidal evaluation of
D-ribose-1-spiro- 5'N[1']-β-2'-thiohydantoin and
D-ribose-1-spriro- 5'N[1']-α-2'-thiohydantoin The postemergence herbicidal activity of the compounds of the present invention is demonstrated by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 acetone/water mixtures containing 0.5% TWEEN® 20, a polyoxyethylene sorbitan monolaurate surfactant of Atlas Chemcial Industries, in sufficient quantity to provide the equivalent of about 0.50 kg to 1.0 kg per hectare of active compound when applied to the plants through a spray nozzle operating at 40 psi for a predetermined time. After spraying, the plants are placed on greenhouse benches and cared for in the manner commensurate with conventional greenhouse practices. From 4 to 5 weeks after treatment, the seedling plants, are examined and rated according to the rating system provided below. The data obtained are recorded in Table I below.

| Rating System | | |
|---|---|---|
| RATING | MEANING | % CONTROL COMPARED TO CHECK |
| 9 | COMPLETE KILL | 100 |
| 8 | APPROACHING COMPLETE KILL | 91–99 |

| Rating System | | |
|---|---|---|
| RATING | MEANING | % CONTROL COMPARED TO CHECK |
| 7 | GOOD HERBICIDAL EFFECT | 80–90 |
| 6 | HERBICIDAL EFFECT | 65–79 |
| 5 | DEFINITE INJURY | 45–64 |
| 4 | INJURY | 30–44 |
| 3 | MODERATE EFFECT | 16–29 |
| 2 | SLIGHT EFFECT | 6–15 |
| 1 | TRACE EFFECT | 1–5 |

TABLE I

| | Postemergence Herbicidal Evaluation | | | | | | |
|---|---|---|---|---|---|---|---|
| Test Compound | Rate (kg/ha) | Barn-yard Gr | Large crab | Green fox | Quack grass | Ivy Mr ngly | Rag Weed |
| D-ribose-1-spiro-5'N<sup>1'</sup>-beta(and alpha)-2'-thiohydantoin | 1.0 | 4 | 6 | 7 | 6 | 5 | 7 |
| | 0.5 | 2 | 5 | 6 | 4 | 4 | 6 |

| Rating System | | |
|---|---|---|
| RATING | MEANING | % CONTROL COMPARED TO CHECK |
| 0 | NO EFFECT | 0 |

| Plant Species Used | | |
|---|---|---|
| COLUMN HEADING | COMMON NAME | SCIENTIFIC NAME |
| Barnyardgr | Barnyard Grass | *ECHINOCHLOA CRUSGALLI*, (L)BEAU |
| Large Crab | Crabgrass, Large | *DIGITARIA SANGUINALIS*, (L)SCOP |
| Green Fox | Foxtail, Green | *SETARIA VIRIDIS*, (L)BEAUV |
| Quackgrass | Quackgrass | *AGROPYRON REPENS*, (L) BEAUV |
| Ivy Mrngly | Morning-glory, Ivyleaf | *IPOMOEA HEDERACEA*, (L) JACQ |
| Ragweed | Ragweed, Common | *AMBROSIA ARTEMISIIFOLIA*, L |

What is claimed is:

1. An intermediate compound of formula IV

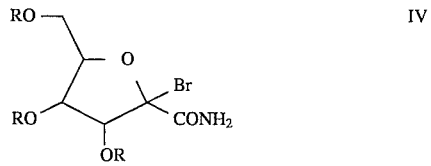

IV wherein R is a protecting group, the optical isomers thereof and the diastereomers thereof.

2. The compound according to claim 1 wherein R is benzoyl or acetyl.

3. The compound according to claim 1 having the isomeric structure

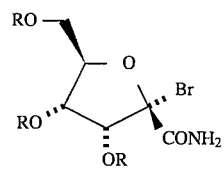

* * * * *